United States Patent [19]

Blezard et al.

[11] Patent Number: 5,223,644
[45] Date of Patent: Jun. 29, 1993

[54] NITROSAMINE INHIBITION

[75] Inventors: Michael Blezard; Glyn R. Jones, both of Whitehaven, England

[73] Assignee: Albright & Wilson Limited, West Midlands, England

[21] Appl. No.: 829,982

[22] Filed: Feb. 3, 1992

[30] Foreign Application Priority Data

Feb. 2, 1991 [GB] United Kingdom ................. 9102311

[51] Int. Cl.$^5$ ........................................... C07C 209/00
[52] U.S. Cl. ...................................... 564/2; 544/173; 544/383; 546/347; 548/348.1; 548/349.1; 548/350.1; 548/347.1; 560/155; 560/205; 560/250; 564/4; 564/5; 564/6; 564/197; 564/298; 564/301

[58] Field of Search ................. 564/2, 4, 298, 301, 564/5, 6, 197; 544/173, 383; 546/347; 548/337; 560/155, 205, 250

[56] References Cited

U.S. PATENT DOCUMENTS

| | | | |
|---|---|---|---|
| 3,333,000 | 7/1967 | Albert et al. | 564/298 |
| 3,441,508 | 4/1969 | Drew et al. | 252/137 |
| 3,463,817 | 8/1969 | Mahnken | 260/583 |
| 4,273,937 | 6/1981 | Gum et al. | 564/2 |

Primary Examiner—Richard L. Raymond
Assistant Examiner—P. O'Sullivan
Attorney, Agent, or Firm—Frishauf, Holtz, Goodman & Woodward

[57] ABSTRACT

Bicarbonates and/or carbonates are used in greater than catalytic amounts to inhibit the formation of nitrosamines during the preparation, storage and/or use of amine oxides.

17 Claims, No Drawings

NITROSAMINE INHIBITION

The present invention relates to a method of inhibiting the formation of nitrosamines, especially during the preparation and/or storage of amine oxides, an amine oxide composition containing a stabiliser and an improved process for the preparation of tertiary amine oxides.

Amine oxides are conventionally prepared by reacting a tertiary amine with hydrogen peroxide. In order to complete the reaction within a commercially acceptable time it is necessary to heat the reaction mixture and/or to employ a catalyst. Since excessive heating tends to cause (or accelerate) the decomposition of peroxide, the use of a catalyst is preferred.

It has been suggested, e.g. in U.S. Pat. No. 3,333,000 that a mixture comprising sodium bicarbonate in concentrations of from 0.02 to 2% by weight of the amine together with sodium pyrophosphate will catalyse the reaction. In practice, concentrations of bicarbonate in the lower part of the range, i.e. below 1% by weight of the amine were found sufficient to catalyse the reaction and higher concentrations were avoided, so as not to leave any substantial residue of bicarbonate in the product.

Subsequently it has been found that carbon dioxide is a very effective catalyst and its use has now replaced that of sodium bicarbonate (see, for instance, GB 2 032 422, FR 2 632 638 or U.S. Pat. No. 4,247,480).

It has been recognised for some years that nitrosamines, which are widely regarded as being potentially harmful, are commonly present as minor, but undesirable, trace contaminants of amine oxides. These contaminants are conventionally present in commercial amine oxides at very low levels of between 200 and 1000 parts per billion.

Such levels have hitherto been close to, or below the limits of detection. However improved analytical methods have now made it possible to detect nitrosamines reliably in amine oxides at concentrations below 50 ppb and generally down to 10 ppb total NO.

This has led to a pressing demand for amine oxides with less than 50 ppb total NO. None of the methods described hitherto have achieved such levels. It should be noted in this context that the analyses quoted in certain prior literature, e.g. U.S. Pat. No. 4 889 954 relate only to certain specified nitrosamines rather than total NO. The method generally recommended in the prior art for reducing the nitrosamine levels has been to carry out the reaction at relatively low temperatures, e.g. below 40° C., using the carbon dioxide catalyst to maintain an adequate reaction rate. We have found in practice, however, that this approach is not generally effective to produce amine oxides with the desired low nitrosamine content, especially when excess of hydrogen peroxide is used, as has been normal practice to avoid products contaminated with substantial residual unreacted amine.

Furthermore, we have found that on storage, especially in warm conditions, or where the product is subsequently heated as part of the procedure for incorporating it into an end formulation, even amine oxide prepared without detectable nitrosamines may undergo some degradation resulting in nitrosamine formation.

THE INVENTION

Our invention has the object of inhibiting the formation of nitrosamines, especially in amine oxides, during preparation and/or subsequent storage or use. We aim to provide freshly prepared amine oxides with nitrosamine contents, measured as total NO, below 100 ppb and preferably below 50 ppb, and to reduce the formation of nitrosamines when such amine oxides are stored or heated.

We have discovered that bicarbonates and/or carbonates, when present in concentrations substantially greater than those hitherto proposed for catalysing the preparation of amine oxides, (i.e. greater than about 2.5% by weight of the amine) specifically inhibit the formation of nitrosamines during preparation, even at relatively high temperatures and/or with a small excess of peroxide. Moreover, the bicarbonate and/or carbonate leaves sufficient residue in the product to inhibit nitrosamine formation therein if the product is stored for extended periods or heated. Our invention provides the use of bicarbonates and/or carbonates to inhibit the formation of nitrosamines, for example, during the preparation, storage and/or use of amine oxides.

In particular our invention provides a composition comprising an amine oxide and from 2.5% to 20% by weight based on the amine content of the amine oxide of a stabiliser comprising a bicarbonate and/or a carbonate.

According to a further embodiment our invention provides a method for the preparation of an amine oxide which comprises reacting a tertiary amine with hydrogen peroxide in the presence of an amount greater than 2.5% by weight based on the weight of the amine of a stabiliser comprising a bicarbonate and/or a carbonate, said amount being sufficient substantially to inhibit nitrosamine formation.

According to a further embodiment our invention provides a method of stabilising an amine oxide in order to inhibit the formation of nitrosamines on storage or heating which comprises adding thereto 2.5% to 20% by weight based on the amine content of the amine oxide of a stabiliser comprising a bicarbonate and/or a carbonate.

The invention is hereinafter described with particular reference to the stabilisation, during and after preparation, of amine oxides, but may also be applicable to inhibition of nitrosamine formation in the context of other reactions and products which involve a nitrosamine hazard, for example alkanolamides.

In the preparation referred to, amine and hydrogen peroxide are mixed in a molar ratio that may typically range from 1:0.9 (amine: hydrogen peroxide) through to 1:1.1. The most preferred ratio is 1:1, i.e. a stoichiometric amount. This is because, on one hand, excess amine over the stoichiometric quantity in the reaction vessel leads to residual free, unreacted amine as a product contaminant, but, moreover, we have discovered that excess hydrogen peroxide, over the stoichiometric quantity is a contributory factor in the formation of nitrosamine impurities.

The presence of a substantial stoichiometric excess of hydrogen peroxide, e.g. more than 0.05%, makes it difficult to obtain low levels of nitrosamine and requires higher levels of stabiliser to achieve nitrosamine levels below 100 ppb.

We have found that no useful inhibition of nitrosamine formation occurs with stabiliser at less than about 2.5% by weight based on the weight of the amine.

Stabiliser levels of 2.5% based on the weight of amine, and above, are generally sufficient to provide and maintain acceptable nitrosamine levels, at least when no substantial stoichiometric excess of hydrogen peroxide is present. However if it is desired to include a substantial excess of hydrogen peroxide, e.g. greater than 0.05% based on the stoichiometric weight, then higher levels of stabiliser may be required, e.g. up to 5% or even 10% based on the weight of amine where stoichiometric excesses of peroxide approaching 0.1% are desired. As a general rule, where an excess of peroxide is present we prefer that the amount of stabiliser should be at least $(2.5+50n)\%$ based on the weight of amine where n is the excess of peroxide expressed as a fraction of the stoichiometric weight.

The stabilizer may suitably comprise a bicarbonate such as sodium bicarbonate. Alternatively other water soluble bicarbonates, e.g. alkali metal bicarbonates such as potassium bicarbonate, lithium bicarbonate, ammonium bicarbonate or alkaline earth metal bicarbonates such as magnesium or calcium bicarbonate may be present.

More preferably, the stabiliser may comprise a carbonate such as an alkalimetal, alkaline earth metal or ammonium carbonate, e.g. sodium, magnesium or calcium carbonate, or a mixture of bicarbonate and carbonate, e.g. in a molar ratio of about 1:1, provided that the pH does not exceed about 10 during preparation of amine oxides (or excessive decomposition of hydrogen peroxide occurs). However, when the stabiliser is added to the product after preparation, such a constraint does not arise and threrefore higher pH's may be tolerated, depending on the desired end use.

Note that references made to "stabiliser" herein are intended to include all the above alternatives.

The preferred proportion of stabiliser, by weight based on the total weight of amine (when added to the reaction mixture) or of the amine content of the amine oxide (when added to the product) is 6 to 10%. No additional benefit, with respect to nitrosamine inhibition, is obtained by increasing stabiliser content above 10%. Moreover, excessive inorganic salt in the reaction vessel or product may be undesirable for some end uses. However there is no technical reason why larger proportions, e.g. up to saturation, should not be used if their presence can be tolerated.

The amines that may be used in the process of our invention are typically linear amines of the general formula $R^1 R^2 R^3 N$, wherein $R^1$, $R^2$ and $R^3$ represent straight or branched chain alkyl groups, alkenyl groups or aralkyl groups which may be the same or different. They may be lower alkyl groups, i.e. of from 1 to 7, preferably 1 to 4, carbon atoms, but in a preferred embodiment of this invention, the tertiary amines may instead be represented by the general formula $(R)_m (R^1)_n N$, wherein $m=1$ or 2 and $n=(3-m)$.

The R groups, which may be the same or different, represent in this case $C_8$-$C_{24}$ alkyl or alkenyl polyalkyleneoxy groups, $C_7$-$C_{23}$ esteralkyl or alkenyl groups, amidoalkyl or alkenyl groups, and the $R^1$ groups, which may also be the same or different, represent $C_1$-$C_4$ alkyl, alkoxy or hydroxyalkyl, or polyalkyleneoxy groups.

The alkyleneoxy groups are preferably polyethyleneoxy groups or polypropyleneoxy or mixed ethyleneoxy propyleneoxy groups containing between 1 and 20 ethyleneoxy and/or propyleneoxy groups. The amidoalkyl groups are preferably $C_7$-$C_{23}$ alkyl or alkenyl-amidopropyl groups.

The amines may alternatively comprise cyclic amines such as imidazolines or pyridines, N-substituted piperazines, or N-substituted morpholines, e.g. N-methyl morpholine.

The process of this invention is typically carried out in aqueous solution. Optionally, a sequestrant such as EDTA may be used in the preparation which prevents decomposition of the hydrogen peroxide by chelating the metal ions which catalyse its decomposition. Alternative sequestrants include other chelating agents such as pyrophosphate and phosphonate.

The required concentration of product depends on the particular tertiary amine starting material employed, since those that are preferred for this invention give rise to oxide products with surfactant properties which form a mobile $L_1$ phase at concentrations up to about 30% by weight based on total weight of reaction mixture, subject to exact chemical nature. At higher concentrations the amine oxide products tend to form an immobile M phase. Preferably, water is added to the reaction vessel in the form of aqueous hydrogen peroxide such that the final concentration of product attained is mobile. It is possible at very high concentrations, e.g. 60 to 80% amine oxide (by weight based on total weight of reaction mixture) to form a mobile G phase. This option is, however, less practical in terms of a large-scale reaction scheme and consequently the most preferred embodiment is the most concentrated $L_1$ phase attainable, usually about 30% by weight based on total weight of reaction mixture. Higher concentrations may be achieved in the presence of phase modifiers such as solvents, cosurfactants, hydrotropes or electrolyte salts. On a large scale, temperature rise may be a problem during the reaction, as conditions become closer to adiabatic, hence the use of heel of amine oxide product is preferable since this limits the extent of the exotherm, by avoiding the induction period as the system passes from 2 phase to 1 phase.

The inventors have found that, in the presence of bicarbonate and/or carbonate in the proportions specified above, temperature need not be such a crucial factor in limiting the formation of nitrosamines as by-products as is implied by the prior art, wherein it is stated (e.g. European Pat. Appn. 88306270.3) that in order to inhibit the formation of nitrosamines the preparation of amine oxide must be conducted at 45° C. or lower; most preferably below 30° C. This then necessitates the usage of a promoter to raise the slow reaction rate.

The essence of the present invention is the inhibitory action of the bicarbonate and/or carbonate stabiliser towards nitrosamine formation, thus overriding the necessity to keep the temperature low, during the preparation and/or the storage of amine oxides. Accordingly, the temperature of the reaction vessel when carrying out the process of this invention may range from 2° C. to 85° C., the most preferred temperature range being 30° C. to 50° C. and a typical operating temperature being 40° C. The time to completion of the reaction is generally up to four hours.

Similarly, incorporation of bicarbonate and/or carbonate in the amount specified above, into an existing product renders it heat resistant with respect to the formation of nitrosamine impurities. The inventors have found that this effect is apparent even when the above mentioned product was not originally made in the presence of bicarbonate and/or carbonate.

The embodiments of this invention and its advantages are further illustrated by the following, non-limiting Examples:

EXAMPLES 1-3

Amine Oxide Preparation in the Presence of Sodium Bicarbonate

Method

Lauryl myristyl amine, as EMPIGEN AB (EMPIGEN is a Registered Trade Mark) was weight into a round bottomed flask together with $NaHCO_3$ and $Na_2EDTA$ in the proportions described in the Table 1.

The resulting mixture was warmed to 40° C. with stirring in a water bath. Water and hydrogen peroxide were weighed into separate beakers, in the proportions described in the Table, and half the water was added to the flask containing the amine. The peroxide was added slowly to this flask over a period of 15 minutes and after this time the remaining water was used to wash in the residual peroxide.

The components were allowed to react for a further 4 hours at 40° C. and after this time the free peroxide levels were determined, by addition of a small sample of reaction mixture to acidified potassium iodide and titrating the liberated iodine with standard sodium thiosulphate solution, to give a measure of hydrogen peroxide. A similar experiment was performed in the absence of $NaHCO_3$.

Total nitrosamine contents were determined as total NO by a chemiluminescence method, whereby the sample, after destruction of nitrite ions by sulphuric acid, is denitrosated and the NO gas liberated therefrom is fed into a chemiluminescence analyser. Here it reacts with ozone to give excited $NO_2$. As the $NO_2$ decays to the ground state light is emitted in the near infrared, and this signal may be intergrated electronically. The limit of detection is 10 ppb as NO.

The charge weights are recorded in Table 1 and the results in Table 2.

TABLE 1

| Table of Charge Weights (g) | Ref 1 | Ref 2 | Ref 3 | Ex. 1 | Ex. 2 | Ex. 3 |
| --- | --- | --- | --- | --- | --- | --- |
| EMPIGEN AB | 55.9 | 55.9 | 55.9 | 55.9 | 55.9 | 55.9 |
| 35% (w/w) $H_2O_2$ | 26.4 | 26.4 | 26.4 | 26.4 | 26.4 | 26.4 |
| Water | 117.5 | 117.1 | 116.5 | 115.5 | 113.5 | 111.5 |
| $Na_2EDTA$ | 0.2 | 0.2 | 0.2 | 0.2 | 0.2 | 0.2 |
| $NaHCO_3$ | 0 | 0.4 | 1.0 | 2.0 | 4.0 | 6.0 |
| Moles $H_2O_2$/moles amine | 1.09/1 | 1.09/1 | 1.09/1 | 1.09/1 | 1.09/1 | 1.09/1 |
| $NaHCO_3$/EMPIGEN AB (% w/w based on amine) | 0 | 0.71 | 1.79 | 3.585 | 7.15 | 10.73 |

*EMPIGEN AB Purity assumed = 98.4% for calculating the reaction ratio)
MMW = 221

TABLE 2

| Results | Ref 1 | Ref 2 | Ref 3 | Ex. 1 | Ex. 2 | Ex. 3 |
| --- | --- | --- | --- | --- | --- | --- |
| % $H_2O_2$ (by weight based on total weight sample) | 0.17 | 0.66 | 0.34 | 0.28 | 0.29 | 0.27 |
| "NO" ppb | 314 | 611 | 406 | 237 | 64 | 66 |

It appears that the increased level of bicarbonate reduced the nitrosamine content.

EXAMPLES 4-5

Further work, using the same method as that described in Examples 1-3, but varying the molar ratio of amine to peroxide, gave the following results:

TABLE 3

|  | Example 4 | Example 5 |
| --- | --- | --- |
| % $NaHCO_3$ (w/w, based on weight of amine) | 3.58 | 3.58 |
| Moles peroxide/moles amine | 1.0/1.0 | 0.98/1.0 |
| "NO" ppb | 14 | 13 |

EXAMPLE 6

Inhibition of Nitrosamine Formation in Amine Oxide

Method

3% (by weight based on total weight) $NaHCO_3$ was added to lauryl myristyl amine oxide (as EMPIGEN OB - nominal active 30% w/w). The product was held in a sealed vessel for 14 days at 70° C. in the presence of a control (no $NaHCO_3$). After cooling to R.T. samples were submitted for nitrosamine analysis (method as described in Examples 1-3) together with a sample of the original EMPIGEN OB which had been stored at R.T. The results are recorded in Table 4.

TABLE 4

|  |  | "NO" ppb |
| --- | --- | --- |
| Example 6 | EMPIGEN OB + 3% (by weight based on active weight) $NaHCO_3$ at 70° C. for 14 days | 1,439 |
| Reference 2 | EMPIGEN OB held at R.T. for 14 days | 204 |
| Reference 3 | EMPIGEN OB held at 70° C. for 14 days | 2,631 |

It can be seen that the bicarbonate reduced the formation of nitrosamines by 45%.

EXAMPLE 7

Level of Bicarbonate Residue in Product

Method

The existence of bicarbonate in a product after 4 hour reaction was determined by $CO_2$ evolution and determination, the conditions being shown in Table 5 as follows:

TABLE 5

| Mole ratio $H_2O_2$/amine (EMPIGEN AB) | 1:1 |
| --- | --- |
| Temperature | 45° C. |
| Reaction time | 192 minutes |
| $NaHCO_3$ initally | 3.58% (by weight based on weight amine) |

TABLE 5-continued

| | |
|---|---|
| Mole ratio $H_2O_2$/amine (EMPIGEN AB) | 1:1 |
| $NaHCO_3$ finally | 2.87% (by weight based on weight amine) |

The free peroxide level, as determined by the method described in Examples 1-3, was 0.037% (by weight based on total weight of sample) and hence the reaction was considered to have gone to completion after the above time.

EXAMPLES 8-10

Inhibition of Nitrosamine Formation in Amine Oxide

A plant batch of EMPIGEN OB was treated with the reagents shown below in Table 6 at the concentrations shown. Samples were stored for two weeks at 70° C. and analysed for "NO". pH checks were also made:

TABLE 6

| Conc. of reagent | 0% (Control) | 0.5% | 1.0% | 2.0% | 3.0% |
|---|---|---|---|---|---|
| Example 8 Reagent:$NaHCO_3$ | | | | | |
| "NO", ppb | 10,105 | 11,169 | 8,282 | 6,366 | 7,207 |
| "NO" as % control | — | 110% | 82% | 63% | 71% |
| Example 9 Reagent:$Na_2CO_3$ | | | | | |
| "NO" ppb | 10,105 | 2,323 | 1,676 | 1,464 | 1,414 |
| "NO" as % control | — | 23% | 16.6% | 14.5% | 14% |
| Example 10 Reagent: $NaCO_3/NaHCO_3$ [50/50 w/w] | | | | | |
| "NO", ppb | 10,105 | 3,219 | 2,297 | 2,121 | 1,686 |
| "NO" as % control | — | 32% | 23% | 21% | 17% | pH figures in brackets were obtained before storage of the samples. Control "NO" at the start was 1,176 ppb.

EXAMPLE 11

A plant batch of EMPIGEN OB made without bicarbonate was treated with the reagents shown in Table 7 below and aged for 14 days at 70° C.

TABLE 7

| Reagent | % | Initial "NO" ppb | Final "NO" ppb | "NO" as % control |
|---|---|---|---|---|
| Control | 0 | 1720 | 46,129 | — |
| $NH_4HCO_3$ | 2 | " | 15,306 | 33 |
| $K_2CO_3$ | 2 | " | 1860 | 4 |

Both reagents reduce nitrosamine formation during aging.

We claim:

1. A method of stabilizing an amine oxide in order to inhibit the formation of nitrosamines therein during storage or heating of said amine oxide, said method consisting essentially of adding to said amine oxide before, during or after the preparation thereof from 2.5% to 20% by weight (based on the weight of amine reacted to form said amine oxide) of a stabiliser selected from the group consisting of bicarbonates, carbonates and mixtures of said bicarbonates and carbonates.

2. The method of claim 1, in which said amine oxide is produced by reacting a tertiary amine with hydrogen peroxide in the presence of from 2.5% to 20% by weight (based on the weight of said amine) of said stabiliser.

3. The method of claim 2, in which said tertiary amine has the general formula $R^1R^2R^3N$, wherein $R^1$, $R^2$ and $R^3$, which may be the same or different, are each selected from the group consisting of straight chain alkyl groups, branched chain alkyl groups, straight chain alkenyl groups, branched chain alkenyl groups and aralkyl groups.

4. The method of claim 3, in which said tertiary amine has the general formula $(R)_m(R^1)_nN$, wherein $m=1$ or 2 and $n=(3-m)$, the R groups, which may be the same or different, are each selected from the group consisting of alkyl, alkenyl, alkyl-polyalkyleneoxy and alkenyl-polyalkyleneoxy groups having from 8 to 24 carbon atoms; esteralkyl, esteralkenyl, amidoalkyl, amidoalkenyl, alkyl-amidopropyl, and alkenyl-amidopropyl groups having from 7 to 23 carbon atoms, and the $R^1$ groups, which may be the same or different, are each selected from the group consisting of alkyl, alkoxy, hydroxyalkyl and polyalkyleneoxy groups having from 1 to 4 carbon atoms.

5. The method of claim 2, in which said tertiary amine is a cyclic amine.

6. The method of claim 5, in which said tertiary amine is one selected from the group consisting of imidazolines, pyridines, N-substituted morpholines, and N-substituted piperazines.

7. The method of claim 2, 3, 4, or 5, in which the molar ratio of said amine to said hydrogen peroxide is from 1:0.9 to 1:1.1.

8. The method of claim 7, in which said molar ratio of amine to hydrogen peroxide is about 1:1.

9. The method of claim 1, in which said stabiliser consists essentially of a bicarbonate selected from the group consisting of alkali-metal bicarbonates, alkaline-earth metal bicarbonates and ammonium bicarbonate.

10. The method of claim 9 in which said stabiliser consists essentially of a bicarbonate selected from the group consisting of sodium bicarbonate, potassium bicarbonate, magnesium bicarbonate and calcium bicarbonate.

11. The method of claim 1, in which the proportion of said stabiliser is from 6 to 10% by weight based on total weight of said amine.

12. The method of claim 1, in which said stabiliser also includes a carbonate selected from the group consisting of alkali metal carbonates, alkaline earth metal carbonates and ammonium carbonate.

13. The method of claim 12, in which said carbonate is one selected from the group consisting of sodium carbonate and potassium carbonate, added to said amine oxide after the preparation thereof.

14. The method of claim 12, in which said stabiliser consists essentially of sodium bicarbonate and sodium carbonate in a molar ratio of about 1:1.

15. The method of claim 1, said method being carried out at a temperature of from 2° C. to 85° C.

16. The method of claim 15, in which said temperature is from 30° C. to 50° C.

17. The method of claim 15 or 16, in which said temperature is about 40° C.

* * * * *